US010568545B2

(12) United States Patent
Peru et al.

(10) Patent No.: US 10,568,545 B2
(45) Date of Patent: Feb. 25, 2020

(54) SYSTEM AND METHOD FOR MEASURING COLOR OR SHADE OF AN OBJECT

(71) Applicant: Colgate-Palmolive Company, New York, NY (US)

(72) Inventors: Deborah Ann Peru, Lebanon, NJ (US); Hrebesh Molly Subhash, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/047,159

(22) Filed: Jul. 27, 2018

(65) Prior Publication Data

US 2019/0029564 A1    Jan. 31, 2019

Related U.S. Application Data

(60) Provisional application No. 62/538,115, filed on Jul. 28, 2017.

(51) Int. Cl.
| | | |
|---|---|---|
| *A61C 19/04* | (2006.01) | |
| *A61B 5/103* | (2006.01) | |
| *A61B 5/00* | (2006.01) | |
| *G01J 3/02* | (2006.01) | |
| *G01J 3/50* | (2006.01) | |

(Continued)

(52) U.S. Cl.
CPC .......... *A61B 5/1032* (2013.01); *A61B 5/0075* (2013.01); *A61B 5/0088* (2013.01); *A61C 19/04* (2013.01); *A61C 19/10* (2013.01); *G01J 3/0202* (2013.01); *G01J 3/10* (2013.01); *G01J 3/508* (2013.01)

(58) Field of Classification Search
CPC . A61B 5/1032; A61B 5/75; A61B 5/88; G01J 3/10; G01J 3/508
See application file for complete search history.

(56) References Cited

U.S. PATENT DOCUMENTS

| 5,773,835 A | * | 6/1998 | Sinofsky | .............. | A61B 5/0071 250/462.1 |
|---|---|---|---|---|---|
| 6,519,037 B2 | | 2/2003 | Jung et al. | | |

(Continued)

FOREIGN PATENT DOCUMENTS

| WO | 2008/036644 | 3/2008 |
|---|---|---|
| WO | 2017/001779 | 1/2017 |

OTHER PUBLICATIONS

Extended European Search Report issued on co-pending EP Application No. 18185932.3 dated Feb. 18, 2019.

*Primary Examiner* — Maurice C Smith

(57) ABSTRACT

A color or shade assessment system and a method of assessing color or shade of an object. The system may include a color or shade measurement device having a probe portion terminating at a distal end, a light emitter assembly, and a light receiver assembly. Furthermore, a spacer including a sleeve extending from a proximal end to a distal end and defining a passageway may be coupled to the probe portion. The spacer may be alterable between (1) a first state in which the spacer is detached from the probe portion; and (2) a second state in which at least a portion of the probe portion extends into the central passageway of the sleeve and the distal end of the probe portion is located between the proximal and distal ends of the sleeve.

18 Claims, 15 Drawing Sheets

(51) Int. Cl.
*G01J 3/10* (2006.01)
*A61C 19/10* (2006.01)

(56) References Cited

U.S. PATENT DOCUMENTS

| | | | |
|---|---|---|---|
| 6,577,391 B1 * | 6/2003 | Faupel | A61B 5/0059 |
| | | | 356/337 |
| 6,750,971 B2 | 6/2004 | Overbeck et al. | |
| 7,097,450 B2 | 8/2006 | Jung et al. | |
| 7,768,644 B2 * | 8/2010 | Jung | A61C 19/04 |
| | | | 356/402 |
| 7,808,639 B2 | 10/2010 | Overbeck et al. | |
| 8,570,530 B2 | 10/2013 | Liang | |
| 8,848,991 B2 | 9/2014 | Tjioe et al. | |
| 8,992,216 B2 * | 3/2015 | Karazivan | A61B 5/0088 |
| | | | 356/243.8 |
| 2007/0134615 A1 * | 6/2007 | Lovely | A61B 5/0088 |
| | | | 433/29 |
| 2016/0278615 A1 * | 9/2016 | Kawula | A61B 1/00016 |
| 2017/0000591 A1 | 1/2017 | Guillot et al. | |
| 2017/0027503 A1 * | 2/2017 | Sachse | A61B 1/018 |
| 2017/0311789 A1 * | 11/2017 | Mulcahey | A61F 7/007 |

* cited by examiner

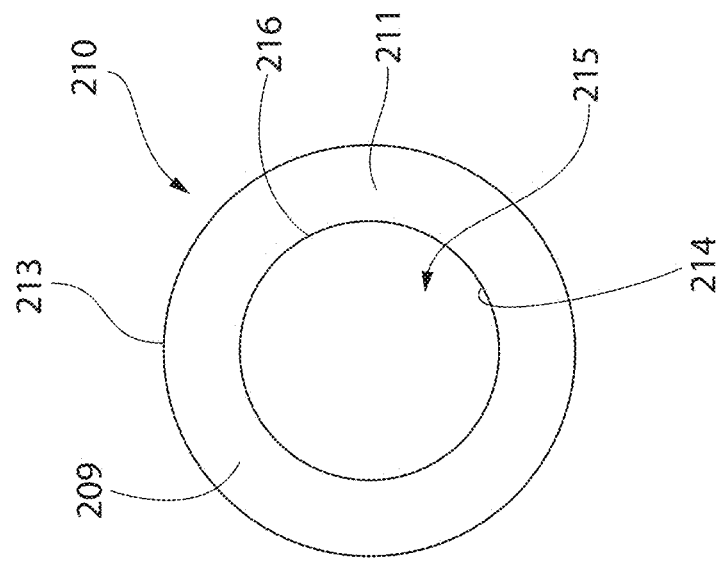
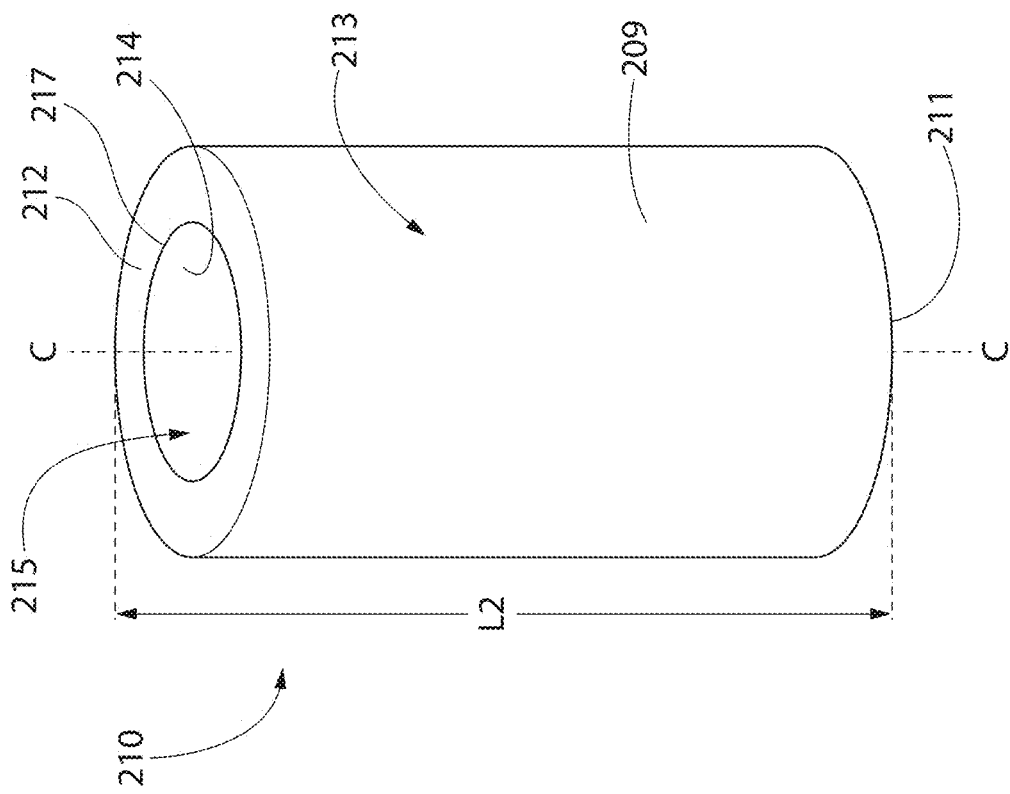
FIG. 8
FIG. 7

| Before Treatment | | | | | | | | |
|---|---|---|---|---|---|---|---|---|
| Pathlength, mm | 0 | 2 | 2.5 | 3 | 3.5 | 4 | 4.5 | 5 | Examiner, Ext. BLG Shade |
| Baseline Sam 1 | 13 | 16.5 | 12.5 | 15 | 15 | 13.5 | 13.5 | 15.5 | 15 |
| Baseline Sam2 | 19.5 | 18.3 | 15.5 | 16.5 | 17 | 19.3 | 18 | 19 | 19 |
| Baseline Sam 3 | 22 | 21 | 19 | 19 | 19 | 18.5 | 19.5 | 19 | 21 |

| After Treatment | | | | | | | | |
|---|---|---|---|---|---|---|---|---|
| Pathlength, mm | 0 | 2 | 2.5 | 3 | 3.5 | 4 | 4.5 | 5 | Examiner, Ext. BLG Shade |
| After Sam1 | 17 | 13.5 | 11.3 | 10 | 9.3 | 8.3 | 9.5 | 8 | 10 |
| After Sam 2 | 21 | 17.5 | 14.8 | 15.2 | 14.5 | 15 | 15.7 | 17 | 16 |
| After Sam3 | 21.5 | 17.2 | 13 | 12.5 | 15 | 12.5 | 13 | 12 | 14 |

FIG. 17

SYSTEM AND METHOD FOR MEASURING COLOR OR SHADE OF AN OBJECT

CROSS-REFERENCE TO RELATED APPLICATIONS

This application claims priority to U.S. Provisional Patent Application No. 62/538,115, filed Jul. 28, 2017, which is incorporated herein by reference.

BACKGROUND

A need has been recognized for devices, systems, and methods for measuring the color, shade, or other optical characteristics of teeth and other objects, particularly in the field of dentistry. Most notably, before installing a dental prosthesis, dentists and other oral health personnel will measure the shade of teeth that are adjacent to where the dental prosthesis will be placed to ensure that the shade of the dental prosthesis matches the shade of the teeth that are adjacent thereto. Recent improvements in tooth whitening have resulted in tooth whitening formulations that whiten the exterior surface of the teeth only. Typical devices that are used to measure tooth shade are unable to detect the results of tooth whitening using such tooth whitening formulations because they measure the shade of the tooth at some optical depth below the exterior surface of the tooth. Thus, a need exists for a system for measuring the color or shade of an object such as teeth that overcomes the aforementioned deficiencies.

BRIEF SUMMARY

The present invention is directed to a color or shade measurement device, such as a spectrophotometer or the like, that can take color or shade measurements at different depths of on object. Specifically, a spacer may be coupled to the color or shade measurement device to modify the depth at which light that is emitted therefrom penetrates into an object for which color or shade is being measured.

In one aspect, the invention may be a tooth assessment system comprising: a color or shade measurement device comprising: a probe portion terminating at a distal end; a light emitter assembly configured to generate and emit light from the distal end of the probe portion; a light receiver assembly configured to receive a portion of the light that has been emitted from the distal end of the probe portion and returned to the distal end of the probe portion as received light and generate data indicative of a color or a shade based on the received light; a spacer detachably coupled to the probe portion so as to be alterable between a first state in which the spacer is detached from the probe portion and a second state in which the spacer is coupled to the probe portion and protrudes beyond the distal end of the probe portion; and wherein the spacer and the light emitter assembly are configured such that: (1) in the first state, the light emitted from the distal end of the probe portion penetrates into both an enamel layer and a dentin layer of a tooth when the distal end of the probe portion is placed into contact with the tooth; and (2) in the second state, the light emitted by the distal end of the probe portion does not penetrate beyond the enamel layer of the tooth when a distal end of a spacer is placed into contact with the tooth.

In another aspect, the invention may be a tooth assessment system comprising: a color or shade measurement device comprising: a probe portion terminating at a distal end; a light emitter assembly configured to generate and emit light from the distal end of the probe portion; a light receiver assembly configured to receive a portion of the light that has been emitted from the distal end of the probe portion and returned to the distal end of the probe portion as received light and generate data indicative of a color or a shade based on the received light; a spacer comprising a sleeve extending from a proximal end to a distal end and defining a central passageway, the spacer alterable between: (1) a first state in which the spacer is detached from the probe portion; and (2) a second state in which at least a portion of the probe portion extends into the central passageway of the sleeve and the distal end of the probe portion is located between the proximal and distal ends of the sleeve.

In yet another aspect, the invention may be a method of assessing tooth color or shade, the method comprising: a) providing a color or shade measurement device comprising: a probe portion terminating at a distal end; a light emitter assembly configured to generate and emit light from the distal end of the probe portion; and a light receiver assembly configured to: (1) receive a portion of the light that has been emitted from the distal end of the probe portion and returned to the distal end of the probe portion as received light; and (2) generate data indicative of a color or a shade based on the received light, wherein when the distal end of the probe portion is placed into contact with the tooth and the light emitter assembly is activated, the light emitted by the distal end of the probe portion penetrates into both an enamel layer and a dentin layer of a tooth; b) coupling a spacer to the probe portion so that the spacer protrudes beyond the distal end of the probe portion; c) contacting a surface of a tooth with a distal end of the spacer and activating the light emitter assembly such that the light emitted from the distal end of the probe portion does not penetrate beyond the enamel layer of the tooth; d) receiving, with the light receiver assembly, at least a portion of the light emitted in step c); and e) generating data indicative of a color or a shade of the tooth based on the light received in step d).

In a further aspect, the invention may be a system for assessing a color or shade of an object, the system comprising: a color or shade measurement device comprising: a probe portion terminating at a distal end; a light emitter assembly configured to generate and emit light from the distal end of the probe portion; a light receiver assembly configured to receive a portion of the light that has been emitted from the distal end of the probe portion and returned to the distal end of the probe portion as received light and generate data indicative of a color or a shade based on the received light; a spacer detachably coupled to the probe portion so as to be alterable between a first state in which the spacer is detached from the probe portion and a second state in which the spacer is coupled to the probe portion and protrudes beyond the distal end of the probe portion; and wherein the spacer is configured such that: (1) in the first state, the light emitted from the distal end of the probe portion penetrates a first average depth into an object when the distal end of the probe portion is placed into contact with the object; and (2) in the second state, the light emitted by the distal end of the probe portion penetrates a second average depth into the object when a distal end of the spacer is placed into contact with the tooth, the first average depth being greater than the second average depth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 7 is a perspective view of a spacer that is configured to be detachably coupled to the probe portion of the color or shade measurement device of FIG. 1;

FIG. 8 is an end view of the spacer of FIG. 7;

FIG. 17 is a table with test results indicating the shade or color of a tooth before and after treatment using the color or shade measurement device with spacers of varying length;

DETAILED DESCRIPTION

Figure 1:
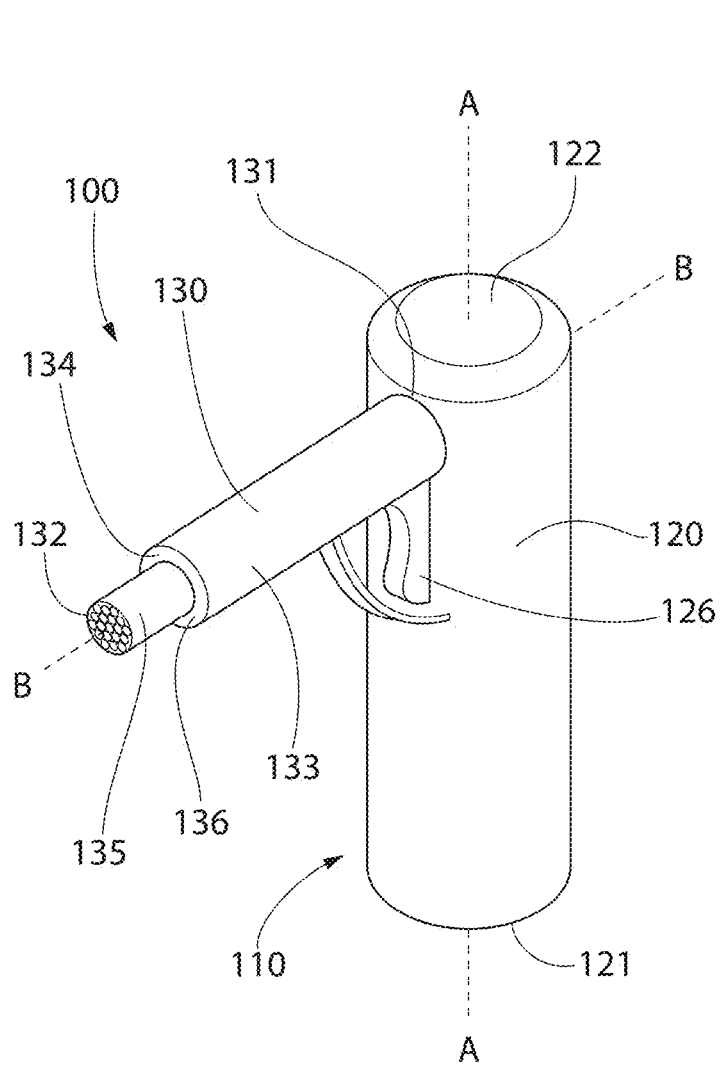
FIG. 1 is front perspective view of a color or shade measurement device in accordance with an embodiment of the present invention.
Figure 2:
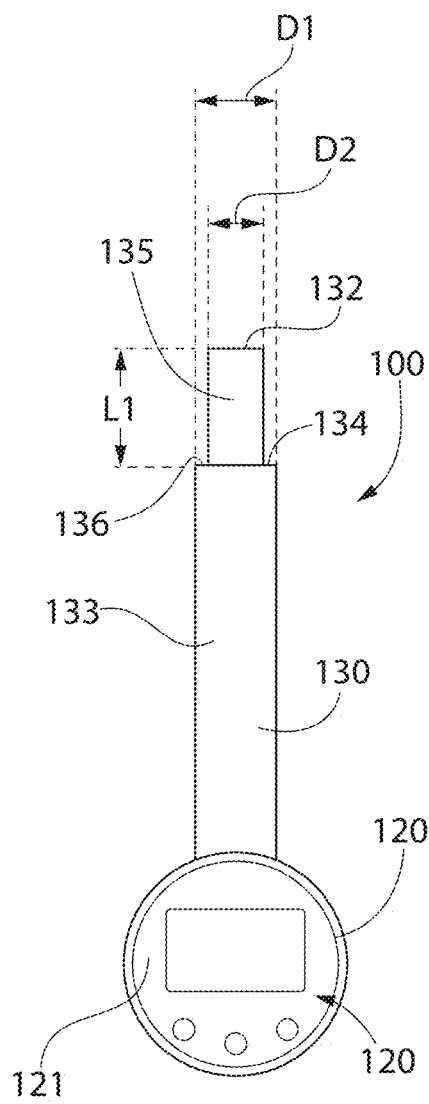
FIG. 2 is a bottom view of the color or shade measurement device of FIG. 1 illustrating a di splay thereof.
Figure 3:
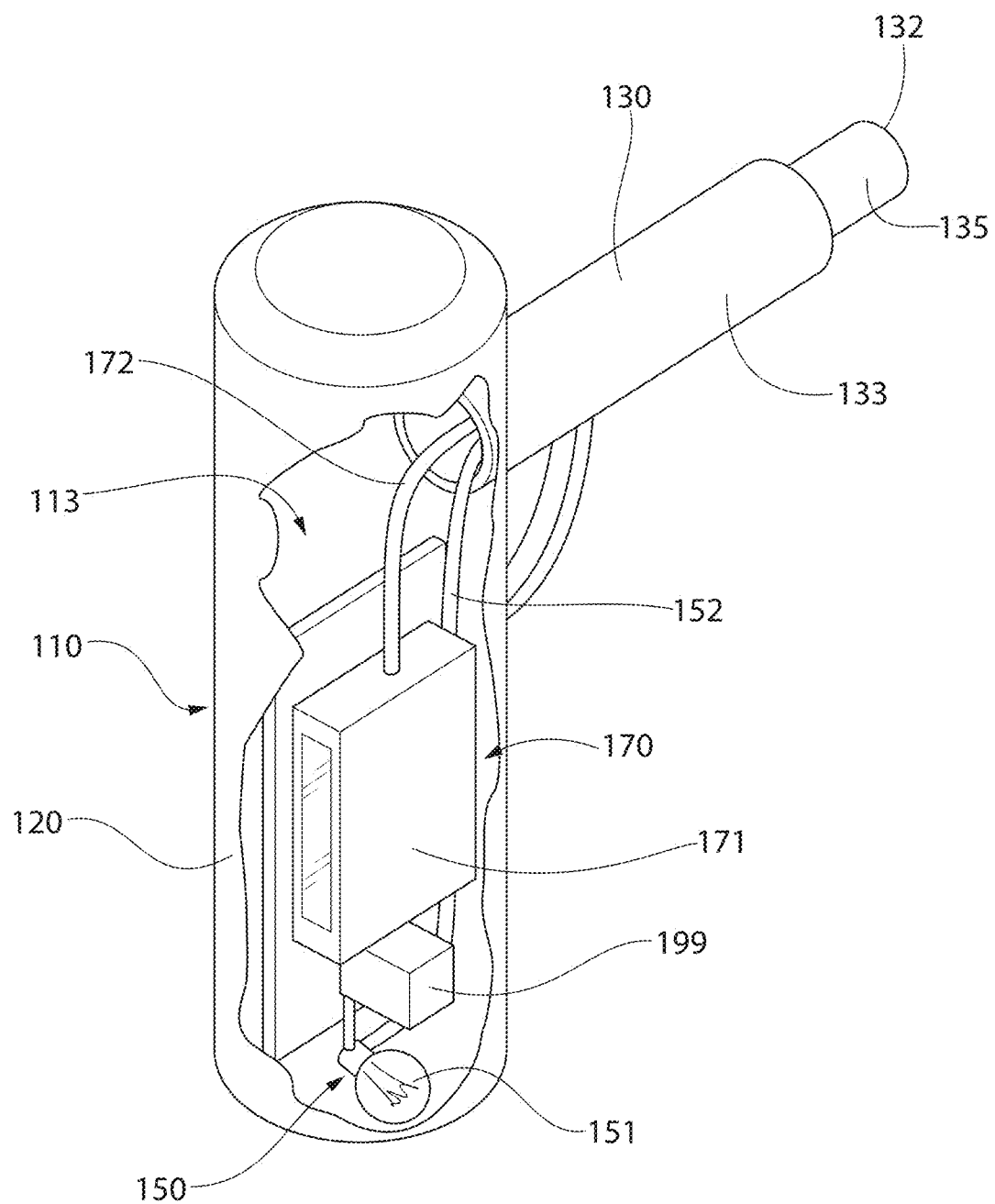
FIG. 3 is a partial cut-away view of the color or shade measurement device of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Referring first to FIGS. 1-6 concurrently, a color or shade measurement device 100 will be described in accordance with an embodiment of the present invention. The color or shade measurement device 100 may in certain embodiments be a spectrophotometer, which is a device that is used to capture and evaluate color. Specifically, the color or shade measurement device 100 transmits light onto an object (such as, for example without limitation, a tooth, skin, or other surface upon which it may be desired to obtain a color or shade measurement) and receives light that is returned to the color or shade measurement device 100 from the object. The returned light is processed by a light receiver assembly (which may comprise a spectrometer) that is configured to generate data indicative of a color, shade, or other optical characteristics of the object based on properties of the returned light. This data can be displayed on a display that either forms a part of the color or shade measurement device 100 or is separate therefrom (such as a monitor, smart phone, laptop, computer, or the like) and operably coupled thereto to display information indicative of the shade, color, or other optical characteristics of the object.

The color or shade measurement device 100 generally comprises a housing 110 having a body portion 120 and a probe portion 130. The housing 110 may be formed of a plastic material and forms an enclosure within which certain electronic components of the color or shade measurement device 100 are positioned. The body portion 120 of the color or shade measurement device 100 extends from a first end 121 to a second end 122 along a first longitudinal axis A-A. The probe portion 130 extends from a proximal end 131 to a distal end 132 along a second longitudinal axis B-B. In the exemplified embodiment, the longitudinal axis B-B of the probe portion 130 is perpendicular to the longitudinal axis A-A of the body portion 120. However, the invention is not to be so limited and the probe portion 130 may be oriented at other angles relative to the body portion 120 or the body and probe portions 120, 130 may be arranged so as to be parallel to one another. Furthermore, the shapes of the body portion 120 and the probe portion 130 are merely exemplary in nature and are not intended to in any way limit the invention. Thus, the body portion 120 and/or the probe portion 130 may have additional contours, rounded features, or the like for added comfort in handling and use. Furthermore, the probe portion 130 may be a continuous structure with the body portion 120 in some embodiments such that the housing 110 is a singular structure having a seamless appearance.

The probe portion 130 of the housing 110 comprises a first portion 133 extending from the body portion 120 to a distal end 134 and a second portion 135 extending from the distal end 134 of the first portion 133 to the distal end 132 of the probe portion 130. The distal end 134 of the first portion 133 forms an annular shoulder 136 that protrudes radially from the second portion 135 of the probe portion 130. In that regard, the first portion 133 of the probe portion 130 has a first minimum diameter D1 and the second portion 135 of the probe portion 130 has a second maximum diameter D2, the first minimum diameter D1 of the first portion 133 being greater than the second maximum diameter D2 of the second portion 135. The second portion 135 of the probe portion 130 also has a first length L1 measured from the distal end 134 of the first portion 133 of the probe portion 130 to the distal end 132 of the probe portion 130. The annular shoulder 136 serves as an abutment feature or a registration feature for a spacer that may be coupled to the probe portion 130 as described more thoroughly below.

In the exemplified embodiment, a display 125 is located on the first end 121 of the body portion 120 of the housing 110. The display is configured to display information indicative of a shade or color of an object being measured to provide that information to a user in a user friendly manner. The display 125 may be located at other positions along the housing 110 in other embodiments. Furthermore, in still other embodiments the display 125 may be a separate structure from the housing 110 that is operably coupled to the color measurement device 100 so that data can be transmitted between the color measurement device 100 and the display 125. In the exemplified embodiment, the color or shade measurement device 100 also includes an actuator 126. The actuator 126 may be located on the body portion 120 of the housing 110 in the location shown or at any other location. Alternatively, the actuator 126 may be located on the probe portion 130 of the housing 110. The actuator 126 may be used to initiate a measurement using the color or shade measurement device 100. In alternative embodiments, the color or shade measurement device 100 may automatically detect when it is in proper positioning to take a measurement and thus it may automatically take measurements without the need for activation of an actuator. In such embodiments, the actuator 126 may be omitted.

The housing 110 defines an internal cavity 113 within which various components of the color or shade measurement device 100 may be located. Specifically, the color or shade measurement device 100 comprises a light emitter assembly 150 and a light receiver assembly 170. The light emitter assembly 150 is configured to generate and emit light from the distal end 132 of the probe portion 130. The light receiver assembly 170 is configured to receive a portion of the light that was previously emitted from the distal end 132 of the probe portion 130 and has since been returned to the distal end 132 of the probe portion 130 as received light. Specifically, the light receiver assembly 170 receives light that is emitted by the light emitter assembly 150 onto an object and reflected, fluoresced, or otherwise returned from the object to the distal end 132 of the probe portion 130.

The light receiver assembly 170 is also configured to generate data indicative of a color or a shade of an object based on the received light. The color measurement device 100 may also include a power source (i.e., battery or the like) 199 operably coupled to the light emitter assembly 150 and/or the light receiver assembly 170. In the exemplified embodiment, the components of the light emitter assembly 150 and the light receiver assembly 170 (described more fully herein below) as well as the power source 199 are located within the internal cavity 113 of the housing 110. However, in alternative embodiments components or parts of one or both of the light emitter assembly 150 and the light receiver assembly 170 may be located external to the internal cavity 113 of the housing 110. Furthermore, the power source 199 may be located outside of the internal cavity 113 in alternative embodiments.

Figure 4:
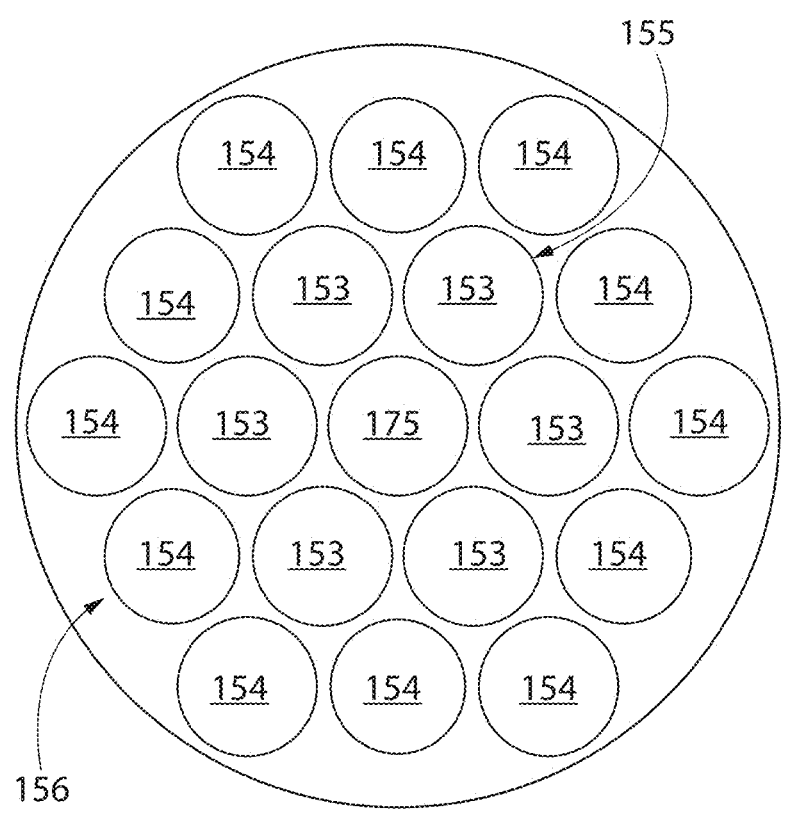
FIG. 4 is a front view of a distal end of a probe portion of the color or shade measurement device of FIG. 1.
Figure 6:
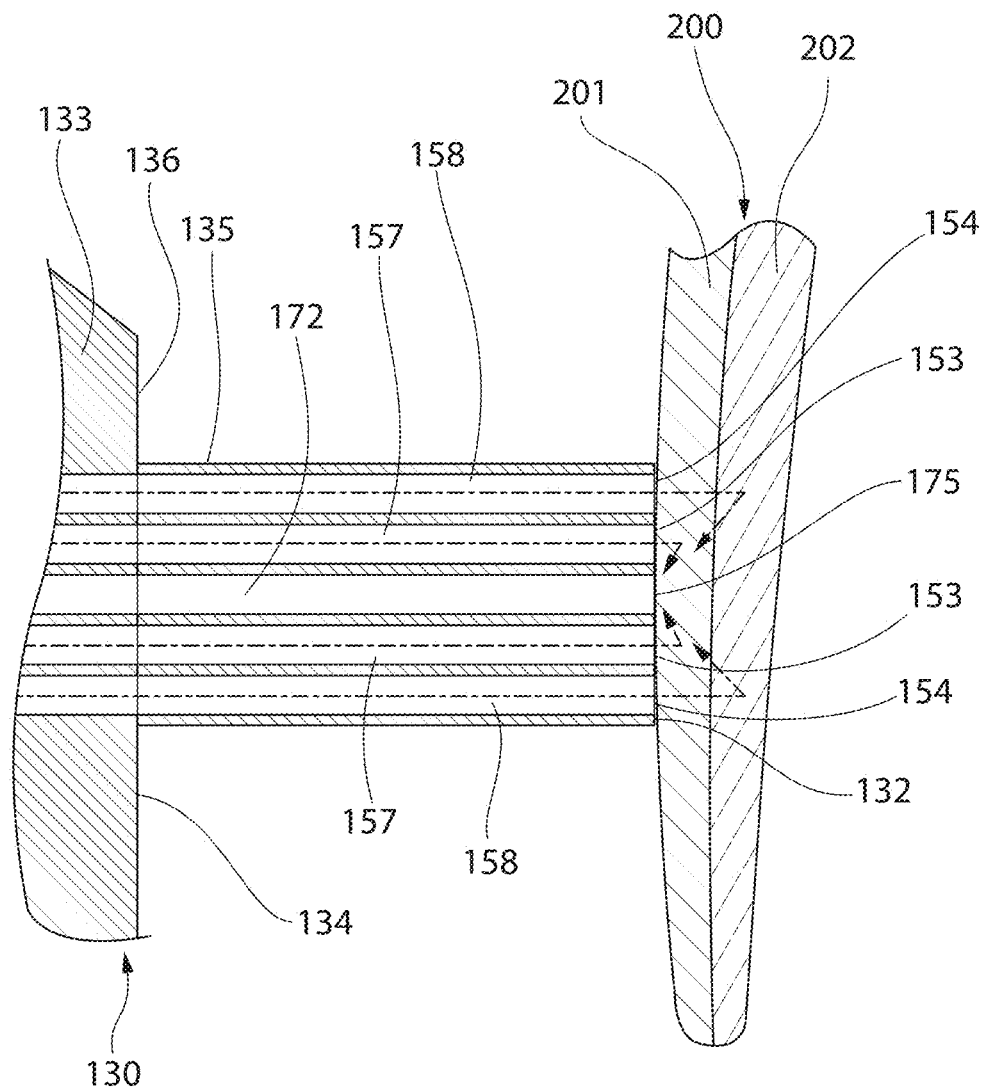
FIG. 6 is a cross-sectional view taken along line VI-VI of FIG. 5.

In the exemplified embodiment, the light emitter assembly 150 comprises a light source 151 and a fiber optic subassembly 152 operably coupled to the light source 151 and extending from the light source 151 to the distal end 132 of the probe portion 130. The fiber optic subassembly 152 carries light from the light source 151 to the distal end 132 of the probe portion 130 where it can be emitted onto a desired object. The fiber optic subassembly 152 is illustrated as a single fiber optic cable in FIG. 3. However, as best shown in FIGS. 4 and 6, the fiber optic subassembly 152 may split out into multiple fiber optic cables 157, 158 so that the distal end of each of the fiber optic cables 157 located at the distal end 132 of the probe portion 130 forms a light emitter that emits light from the distal end 132 of the probe portion 130. Although described herein as being a fiber optic subassembly 152 comprising fiber optic cables, the invention is not to be so limited and the fiber optic subassembly 152 may be any subassembly of components that are configured to carry the light generated by the light source 151 to the distal end 132 of the probe portion 130 where it can be emitted onto a desired object. Thus, the fiber optic cables may be any type of light pipe or other light transfer mechanism that moves light from the light source 151 to the destination or object.

Furthermore, although in the exemplified embodiment the light source 151 is located on the bottom end of the housing portion 120 near the first end 121 of the housing portion 120, the invention is not to be so limited. In other embodiments, the light source 151 may be located at other positions within the internal cavity 113 either in the body portion 120 or even in the probe portion 130 of the housing 110. In still other embodiments, the light source 151 may be located external to the internal cavity 113 such that light from the light source 151 is provided into the housing 110 and then to the distal end 132 of the probe portion 130 via fiber optic cables, a cable assembly, a collection of fiber optics, a light piping system, or the like.

In the exemplified embodiment, the fiber optic subassembly 152 terminates in a first array of light emitters 155 and a second array of light emitters 156. The first array of light emitters 155 comprises a plurality of first light emitters 153, each of which is formed by the terminal end of one of the fiber optic cables 157. The second array of light emitters 156 comprises a plurality of second light emitters 154, each of which is formed by the terminal end of one of the fiber optic cables 158. In the exemplified embodiment, the first and second arrays of light emitters 155, 156 are arranged such that the second array of light emitters 156 surrounds the first array of light emitters 155. Specifically, each of the first and second arrays of light emitters 155, 156 are positioned in a circular arrangement such that the first and second arrays of light emitters 155, 156 are concentric. However, the invention is not to be limited by the position and arrangement of the first and second arrays of light emitters 155, 156 in all embodiments. Thus, different arrangements of the first and second arrays of light emitters 155, 156 are possible in other embodiments.

For example, the plurality of first and second light emitters 153, 154 may be arranged in a random manner in some embodiments. In other embodiments, the plurality of first and second light emitters 153, 154 may not be distinguishable as separate arrays, but may instead merely be a random arrangement of the light emitters that emit light from the distal end 132 of the probe portion 130. The plurality of first and second light emitters 153, 154 may be oriented to emit light at a perpendicular angle onto the surface of the object or at an oblique angle relative to the surface of the object (see FIG. 16A). The plurality of first and second light emitters 153, 154 may be arranged in aligned rows and/or columns, or a random and non-uniform arrangement. Regardless of the exact arrangement of the plurality of first and second light emitters 153, 154, they emit light onto a desired object such that the light is returned to the light receiver assembly 170 as described more fully below.

The light receiver assembly 170 comprises a processing unit 171 and a fiber optic subassembly 172 extending from the distal end 132 of the probe portion 130 to the processing unit 171. The processing unit 171 may be or form a part of a spectrometer in certain embodiments. Thus, the color measurement device 100 may be a spectrophotometer such that the light receiver assembly 170 comprises a spectrometer that includes a processing device. Such a spectrometer will spectrally analyze light returned from the object under test and the data generated by the spectral analysis will be further processed for shade or color or pigment prediction, display of color or spectral data, or the like.

In the exemplified embodiment, the fiber optic subassembly 172 comprises a single fiber optic cable extending from the processing unit 171 to the distal end 132 of the probe portion 130. The fiber optic cable of the fiber optic subassembly 172 terminates in a light receiver 175 at the distal end 132 of the probe portion 130. Of course, in alternative embodiments there may be multiple fiber optic cables and multiple light receivers 175 located at the distal end 132 of the probe portion 130. In the exemplified embodiment, the light receiver 175 is centrally located on the distal end 132 of the probe portion 130 such that the light receiver 175 is surrounded by the first array of light emitters 155. Of course, other locations and positioning of the light receiver 175 relative to the first and second arrays of light emitters 155, 156 are possible in alternative embodiments. Furthermore, there may be multiple light receivers 175 each coupled to the same processing unit 171 or to different processing units as needed to achieve the desired measurement goals.

During use, a user activates the actuator 126 thereby causing the light source 151 of the light emitter assembly 150 to generate light. The generated light is carried or otherwise moved to the distal end 132 of the probe 130 via the fiber optic subassembly 152. The light is then emitted from the distal end 132 of the probe 130 onto a desired object. The light that is emitted is eventually returned including the distal end 132 of the probe 130 as received light. The received light is received by the light receiver 175 and carried or otherwise moved from the light receiver 175 into the processing unit 171 of the light receiver assembly 170. The processing unit 171 generates data indicative of a color or a shade of the object that the light was emitted onto and returned from based on properties of the received light. Specifically, the data may relate to a shade guide value, a paint or other pigment specifier or formulation, pass/fail indication, etc. For example, the processing unit 171 may generate data of a tooth shade in accordance with a tooth shade guide.

The processing unit 171 may in some embodiments comprise a processor and a memory device. The processor and memory device may be separate components or the memory device may be integrated with the processor within the processing unit 171. Furthermore, the processing unit 171 may include only one processor and one memory device, or it may include multiple processors and multiple memory devices. The processor of the processing unit 171 may be any computer or central processing unit (CPU), microprocessor, micro-controller, computational device, or circuit configured for executing some or all of the processes described herein, including without limitation: (1) activating and deactivating the light source 151; and (2) generating data based on the properties of the received light. The memory device of the processing unit 171 may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by the processor which is operably connected thereto. The memory device may store algorithms and/or calculations that can be used (by the processor) to determine the color or shade data based on the received light as described herein.

Referring briefly to FIGS. 5, 6, 16A, and 16B, in one embodiment the color or shade measurement device 100 may be used to measure the shade or color of a tooth 200. As is known in the art, teeth have multiple layers including an enamel layer 201 and a dentin layer 202. The enamel layer 201 is the outermost layer of the tooth 200 that makes up the normally visible part of the tooth. The dentin layer 202 is located beneath the enamel layer 201 such that the dentin layer 202 is normally covered by the enamel layer 201. The enamel layer 201 is generally translucent with a color that varies from light yellow to grayish/bluish and the dentin layer 202 may have a range of color from white to yellow. However, since the enamel layer 201 is semi translucent, the color of the dentin layer 202 strongly affects the appearance of the tooth 200 because it is visible beneath the semi translucent enamel layer 201.

Figure 5:
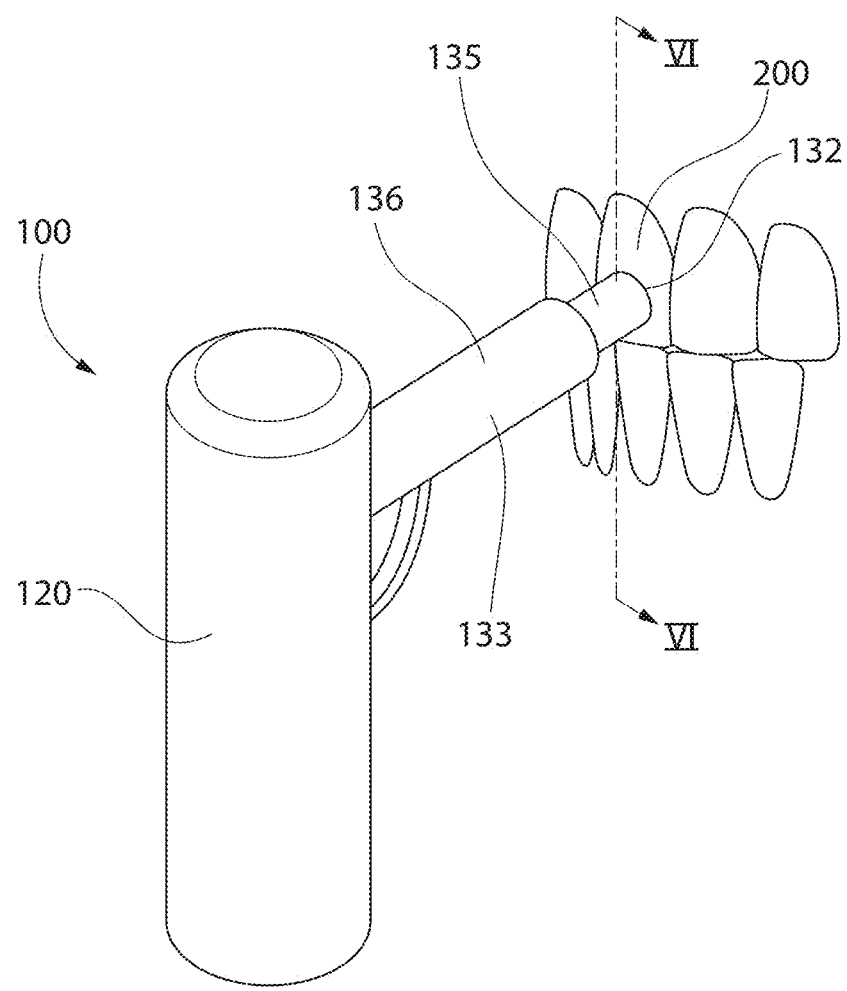
FIG. 5 is a perspective view illustrating the color or shade measurement device of FIG. 1 being used to take a measurement of a shade or color of a tooth.
Figure 16A:
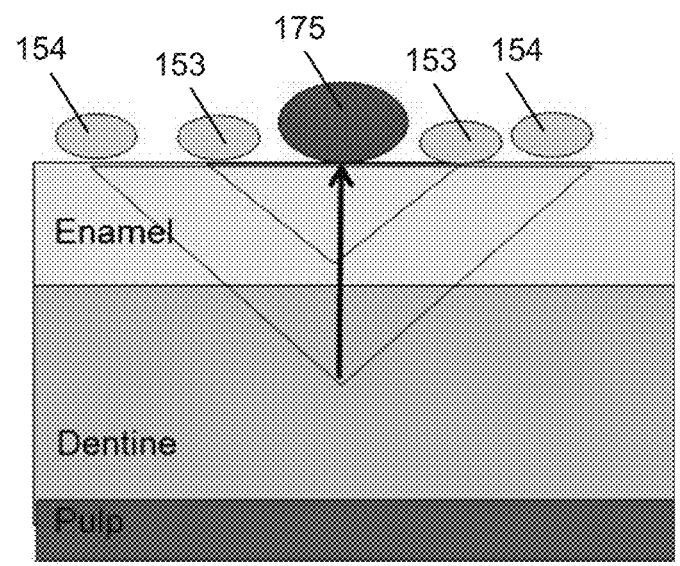
FIGS. 16A and 16B are schematic illustrations of the depth of light penetration into a tooth without a spacer coupled to the color or shade measurement device.
Figure 16B:
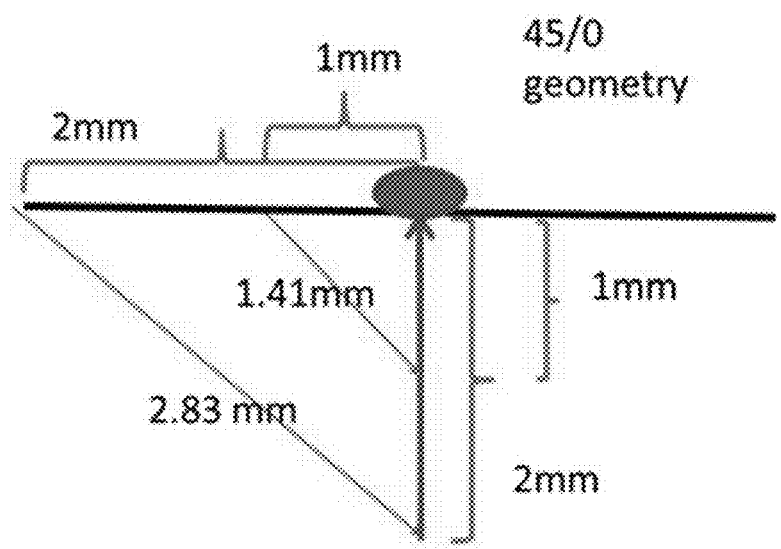

FIGS. 5 and 6 illustrate the color measurement device 100 being used to measure the color or shade of a tooth 200 and FIGS. 16A and 16B illustrate the penetration depth of the light emitted by the first and second light emitters 153, 154. Specifically, to use the color measurement device 100 to measure the shade or color of a tooth 200, the distal end 132 of the probe portion 130 is placed into contact with the tooth 200 being measured. Then, the light emitter assembly 150 is activated to generate and emit light from the distal end 132 of the probe portion 130 onto the tooth 200. As shown, the light emitted from the distal end 132 of the probe portion 130 penetrates into both the enamel layer 201 and the dentin layer 202 of the tooth 200 when the distal end 132 of the probe portion 130 is in contact with the tooth 200 during measurement. As best seen in FIGS. 16A and 16B collectively, the first and second light emitters 153, 154 may be oriented to emit light at an angle onto the tooth 200. The light emitted from the first light emitters 153 may travel approximately 1.41 mm, which equals a depth of about 1 mm into the tooth 200 and the light emitted from the second light emitters 154 may travel approximately 2.8 mm, which equals a depth of about 2 mm into the tooth 200.

Based on the depths of penetration noted above, in the exemplified embodiment the light emitted from the plurality of first light emitters 153 may penetrate into the enamel layer 201 without penetrating into the dentin layer 202 while simultaneously the light emitted from the plurality of second light emitters 153 may penetrate into the dentin layer 202. The difference in level or depth of penetration is based on the location of the first and second light emitters 153, 154 and the angle at which they direct the light towards the tooth 200. Thus, in this embodiment and in this state, the light emitted from the distal end 132 of the probe portion 130 penetrates into both the enamel layer 201 and the dentin layer 202 of the tooth 200 during measurement.

After contacting the tooth 200, a portion of the light that has been emitted from the distal end 132 of the probe portion 130 is then returned to the distal end 132 of the probe portion 130 as received light. The received light is received by the light receiver 175 at the distal end 132 of the probe portion 130 and then carried to the processing unit 171 via the fiber optic subassembly 172. The processing unit 171 then processes the received light and generates data indicative of a color or a shade of the tooth 200 (in accordance with a tooth shade guide) based on the received light. Because the received light is light that has penetrated to both the enamel layer 201 and the dentin layer 202 of the tooth 200, the data generated is based on a combination of shade/color information of the enamel layer 201 and the dentin layer 202. This is acceptable in some instances because, as noted above, due to the translucency of the enamel layer 201, it is the dentin layer 202 that dictates some of the visible shade or color of the teeth. Thus, processing data from light returned from the enamel layer 201 and the dentin layer 202 provides an accurate assessment of the shade or color of the tooth 200.

However, recent developments in tooth whitening formulations and processes have resulted in tooth whitening formulations that are capable of instantaneously whitening the teeth. Such tooth whitening formulations operate in a similar manner to fingernail polish in that they coat the outer surface of the teeth. More specifically, such tooth whitening formulations adhere to the dental enamel to impart an immediate discernable whitening effect to the teeth, thus rapidly altering the color or shade of the surface of the tooth as discerned by a viewer. As can be appreciated, the color measurement device 100 as described herein above would be unable to accurately detect differences in tooth color or shade that occur only in the enamel because at least some of the light that is being used in the tooth color or shade determination is light that is returned from the dentin of the tooth (which is not affected by the instant tooth whitening formulations described in this paragraph). Thus, for purposes of demonstrating the effectiveness of an instant tooth whitening formulation by taking tooth color or shade measurements both immediately before and immediately after application of the instant tooth whitening formulation to the teeth, the color measurement device 100 would not be an effective measurement tool.

Figure 9:
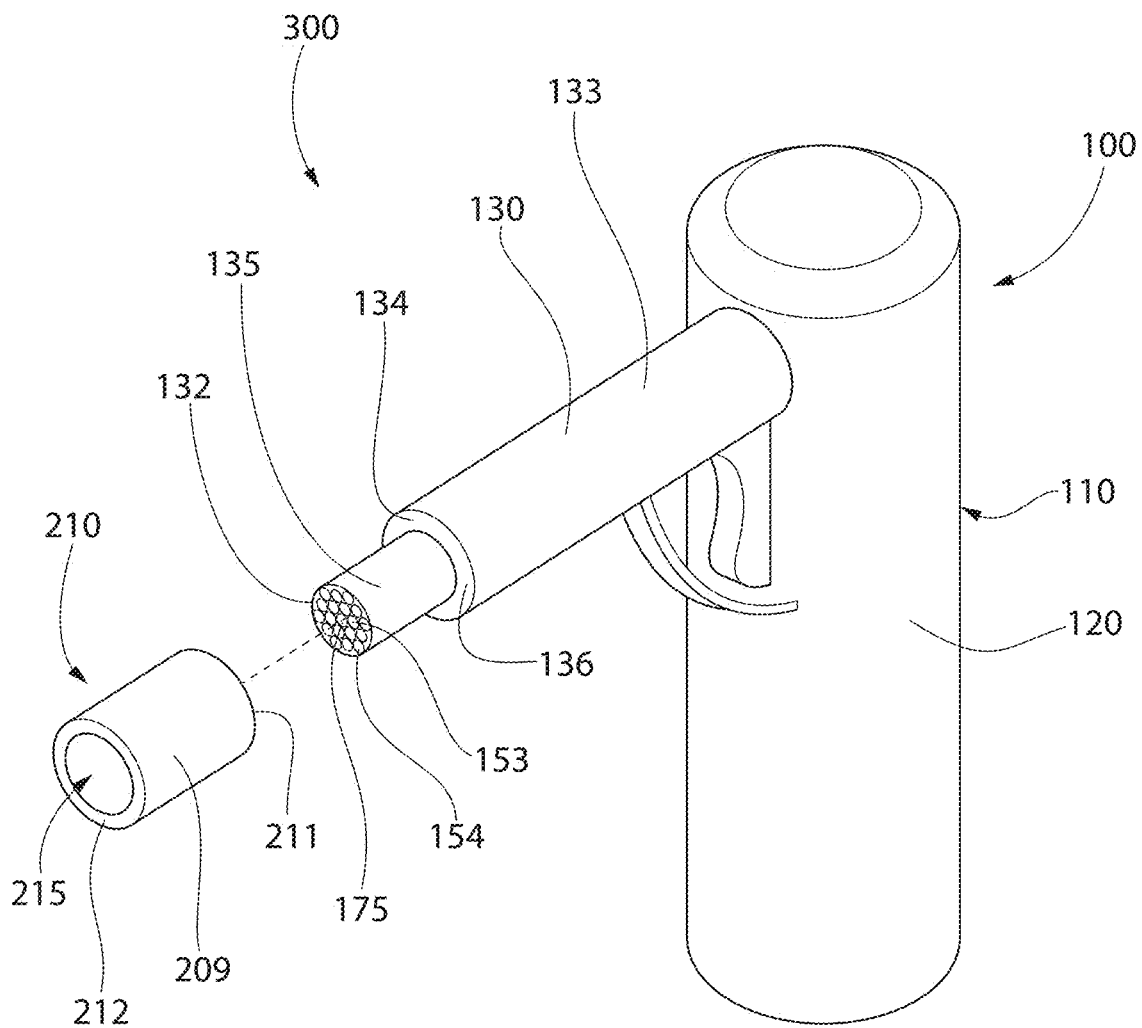
FIG. 9 is a perspective view illustrating the manner of coupling the spacer of FIG. 7 to the color or shade measurement device of FIG. 1.

In that regard, with reference to FIGS. 7-9, in certain embodiments the invention may be directed to a tooth assessment system 300 that comprises the color measurement device 100 described herein above and a spacer 210 that is configured for detachable coupling to the color measurement device 100. Specifically, the spacer 210 is sized and shaped to enable it to be readily attached to and detached from the probe portion 130 of the color/shade measurement device 100. When coupled to the probe portion 130 of the color/shade measurement device 100, the spacer 210 functions to increase the distance between the distal end 132 of the probe portion 130 and the tooth being measured so that the light emitted from the distal end 132 of the probe portion 130 does not penetrate as far as it would were the spacer 210 not coupled to the probe portion 130 of the color measurement device 100. This difference is readily illustrated when viewing FIGS. 6 and 12 in a side-by-side manner.

The spacer 210 comprises a sleeve 209 that extends from a proximal end 211 to a distal end 212 along a third longitudinal axis C-C. The spacer 210 has a second length L2 measured from the proximal end 211 of the sleeve 209 to the distal end 212 of the sleeve 209. The sleeve 209 comprises an outer surface 213 and an inner surface 214. The inner surface 214 defines a central passageway 215 that extends through the entirety of the sleeve 209 from a first opening 216 located at the proximal end 211 of the sleeve 209 to a second opening 217 located at the distal end 212 of the sleeve 209. In the exemplified embodiment, the central passageway 215 has a constant diameter from the proximal end 211 to the distal end 212 of the sleeve 209. Although this is not required in all embodiments, it may impart a better attachment between the spacer 210 and the probe portion 130, which has a constant outer diameter D2 in the exemplified embodiment Referring to FIGS. 9-12 concurrently, the spacer 210 is detachably coupled to the probe portion 130 of the color measurement device 100 so as to be alterable between a first state (FIG. 9) in which the spacer 210 is detached from the probe portion 130 and a second state (FIG. 10) in which the spacer 210 is coupled to the probe portion 130. The spacer 210 is readily transitioned between the first and second states by simply sliding the spacer 210 over the second portion 135 of the probe portion 130 of the color measurement device 100 in opposing directions along the axis C-C (one direction to slide the spacer 210 onto the second portion 135 of the probe portion 130 and the opposite direction to detach the spacer 210 from the second portion 135 of the probe portion 130). Specifically, to couple the spacer 210 to the probe portion 130, the distal end 132 of the probe portion 130 is inserted into the first opening 216 in the proximal end 211 of the sleeve 209 of the spacer 210. The spacer 210 is then translated in a direction of its longitudinal axis C-C until the proximal end 211 of the sleeve 209 of the spacer 210 contacts or abuts against the distal end 134 (i.e., annular shoulder 136) of the first portion 133 of the probe portion 130. Thus, due to the increased diameter of the first portion 133 of the probe portion 130 relative to the second portion 135 of the probe portion 130, the spacer 210 is only able to slide a certain distance onto the probe portion 130 before it is prevented from further sliding by the annular shoulder 136 formed by the distal end 134 of the first portion 133 of the probe portion 130

In the exemplified embodiment, the spacer 210 is coupled to the second portion 135 of the probe portion 130 via frictional engagement between the inner surface 214 of the sleeve 209 and an outer surface 137 of the second portion 135 of the probe portion 130. Specifically, when the spacer 210 is coupled to the second portion 135 of the probe portion 130, the outer surface 137 of the second portion 135 of the probe portion 130 at least partially in surface contact with the inner surface 214 of the sleeve 209 of the spacer 210. The outer diameter of the second portion 135 of the probe portion 130 and the inner diameter of the sleeve 209 of the spacer 210 may be selected to ensure that the spacer 210 may be slid onto the second portion 135 of the probe portion 130 and maintained thereon due to frictional engagement between the outer surface 137 of the second portion 135 of the probe portion 130 and the inner surface 214 of the sleeve 209 of the spacer 210. Of course, frictional engagement is only one connection technique and others are possible including mechanically engaging features (i.e., ribs and grooves), snap-fit, and the like.

In the exemplified embodiment there is no additional locking feature to maintain the spacer 210 on the probe portion 130. Rather, the frictional engagement noted above is the only mechanism used for keeping the spacer 210 positioned on the second portion 135 of the probe portion 130. Of course, locking features could be added to securely retain the spacer 210 on the probe portion 130 in alternative embodiments. These could be mating indents/detents or bumps/grooves, flexible tabs, protuberances and notches, screw threads, or the like. However, in the exemplified embodiment such locking features are not necessary because the frictional engagement between the inner surface 214 of the sleeve 209 and the outer surface 137 of the second portion 135 of the probe portion 130 is sufficient to maintain the sleeve 209 on the second portion 135 of the probe portion 130 under standard operating conditions.

In the exemplified embodiment, the outer diameter of the sleeve 209 is substantially the same as the outer diameter of the first portion 133 of the probe portion 130. This creates a seamless and flush appearance when the spacer 210 is coupled to the probe portion 130. However, the invention is not to be so limited in all embodiments and the outer diameter of the sleeve 209 may be less than or more than the diameter of the first portion 133 of the probe portion 130 in other embodiments.

Figure 10:
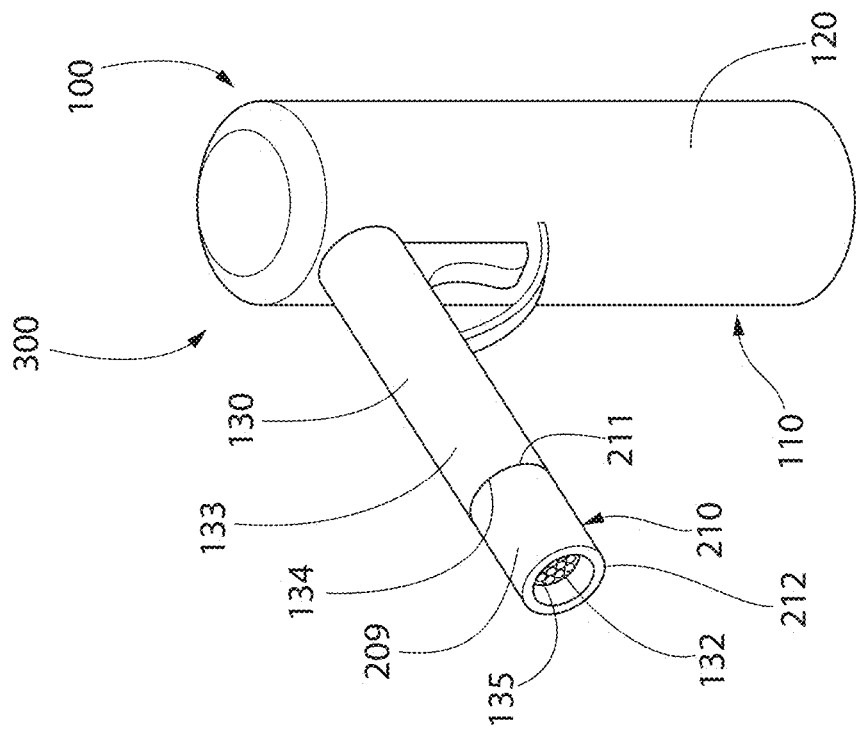
FIG. 10 is a perspective view illustrating the color or shade measurement device of FIG. 1 with the spacer of FIG. 7 coupled thereto.
Figure 12:
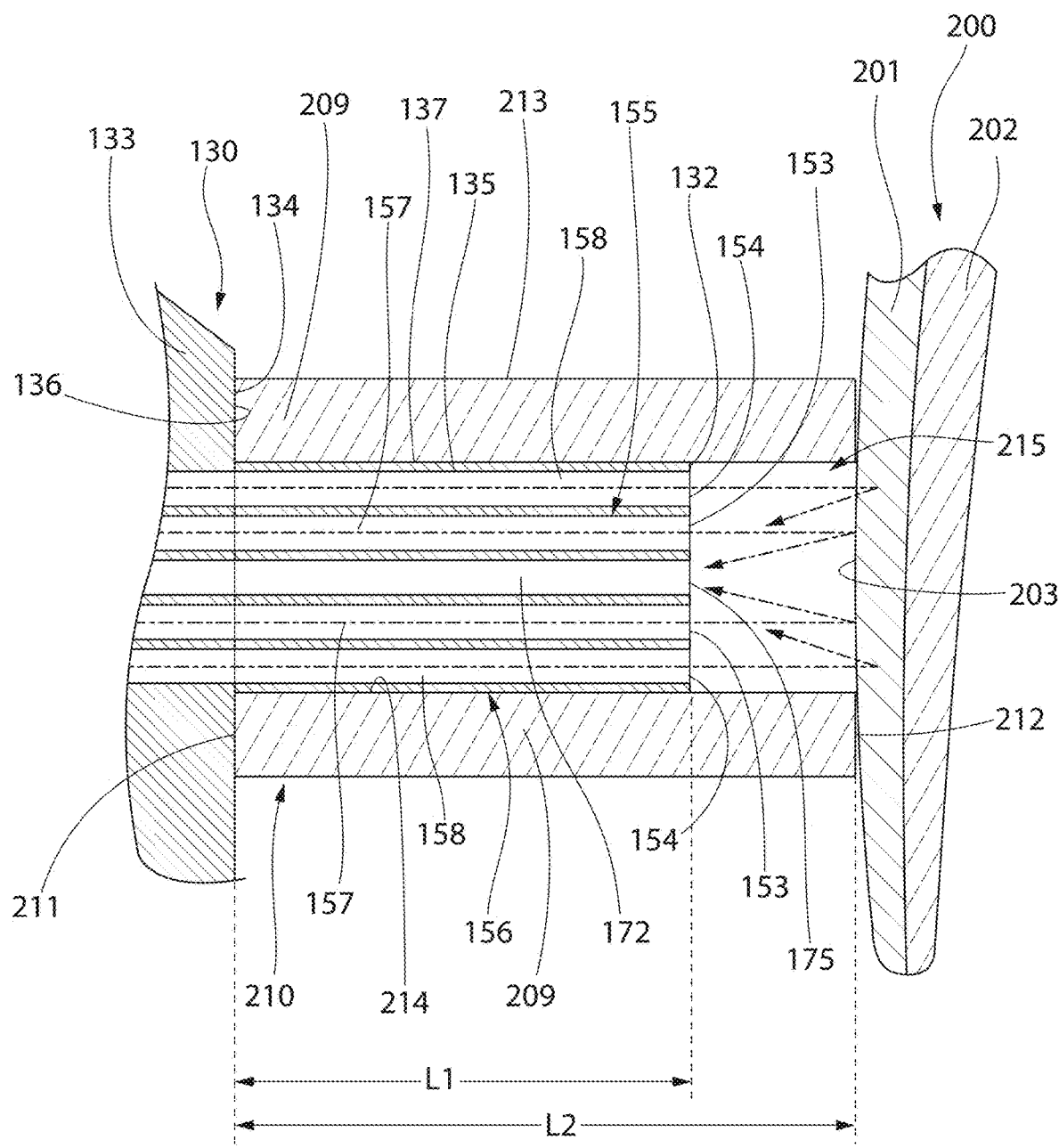
FIG. 12 is a cross-sectional view taken along line XII-XII of FIG. 11.

When the spacer 210 is coupled to the probe portion 130, at least a portion of the probe portion 130 extends into the central passageway 215 of the sleeve 209 and the distal end 132 of the probe portion 130 is located between the proximal and distal ends 211, 212 of the sleeve 209. In the exemplified embodiment, when the spacer 210 is in the second state and coupled to the probe portion 130, the entirety of the probe portion 130 is located within the central passageway 215 of the sleeve 209. This is because the proximal end 211 of the sleeve 209 abuts against the distal end 134 of the first portion 133 of the probe portion 130 and the length L2 of the sleeve 209 is greater than the length L1 of the second portion 135 of the probe portion 130. Thus, in the second state, the distal end 212 of the sleeve 209 protrudes beyond the distal end 132 of the probe portion 130. This is best seen in FIGS. 10 and 12. As a result, in the second state with the spacer 210 attached to the probe portion 130 the light emitting end (i.e., the distal end 132) of the probe portion 130 is spaced further from the tooth 200 during color/shade measurement than if the spacer 210 is not attached. As a result, the penetration depth of the light emitted from the probe portion 130 into the tooth 200 is reduced when the spacer 210 is attached to the probe portion 130 as compared to when the spacer 210 is not attached to the probe portion 130.

In certain embodiments, the length L2 of the spacer 210 may be in a range of 1 cm to 2 cm, more specifically 1.2 cm to 1.8 cm, still more specifically 1.4 cm to 1.6 cm, and still more specifically approximately 1.5 cm. In some embodiments, the difference between L2 and L1 is between 0.1 mm and 5 mm, or between 0.1 and 3 mm, or more specifically between 1 mm and 3 mm, between 1.5 mm and 3 mm, or between 2 mm and 3 mm. In other embodiments the difference between L2 and L1 is between 2 mm and 5 mm. The length of the spacer 210 can be changed depending on desired end use and depending on the length of the second portion 135 of the probe portion 130. In some embodiments the system may include a plurality of the spacers 210, each having a different length. Specifically, the system may include various spacers such that the difference between L2 and L1 is 2 mm, 2.5 mm, 3 mm, 3.5 mm, 4 mm, 4.5 mm, and 5 mm. Additional spacers may also be included. In other embodiments a single spacer having size length adjustment may be used. Such a spacer may be configured to be lengthened or shortened via a telescoping feature or the like and the spacer may be capable of being temporarily locked into various different lengths. Depending on the desired end use and purpose, a different sized spacer (or a spacer having length adjustment capabilities) may be needed. Each of the spacers 210 may be detachably coupled to the probe portion 130 of the color measurement device 100 as described herein. The further the light emitting surface of the probe portion 130 is required to be away from an object under test to obtain desirable results, the larger the spacer that may be used.

Although described herein mostly with regard to uses for measuring tooth shade, the invention is not to be so limited in all embodiments. Objects or surfaces other than teeth can be measured for color or shade using the device described herein with the spacer 210 as an attachment. In some embodiments, the device with the spacer 210 thereon may be used to measure the color of a person's skin. This can have usefulness in the field of dermatology to illustrate the effectiveness of a treatment being used to alter a patient's skin color (either during treatment of a condition, for cosmetic purposes, or for elective purposes). The spacer 210 may operate as a retrofit device to convert the color or shade measurement device 100 into a device that takes color or shade measurements from a first depth within a surface of the object to a device that takes color or shade measurements from a second depth within the surface of the object, the second depth being less than the first depth. In some embodiments, the spacer 210 may be a retrofit device that ensures that the color or shade measurement device 100 takes shade or color measurements only from the exposed outer surface of an object under test.

The spacer 210 may be formed from any of a number of materials including various different types of hard plastic, metal, wood, or the like. However, in certain embodiments the spacer 210 is formed of an opaque material that prevents any ambient light from entering into the central passageway 215 during use of the device in the second state, which could affect measurements made by the device. The spacer 210 may be black in some embodiments, although this is not required in all embodiments. The spacer 210 may be formed via injection molding, 3D printing, extrusion, or the like.

Figure 11:
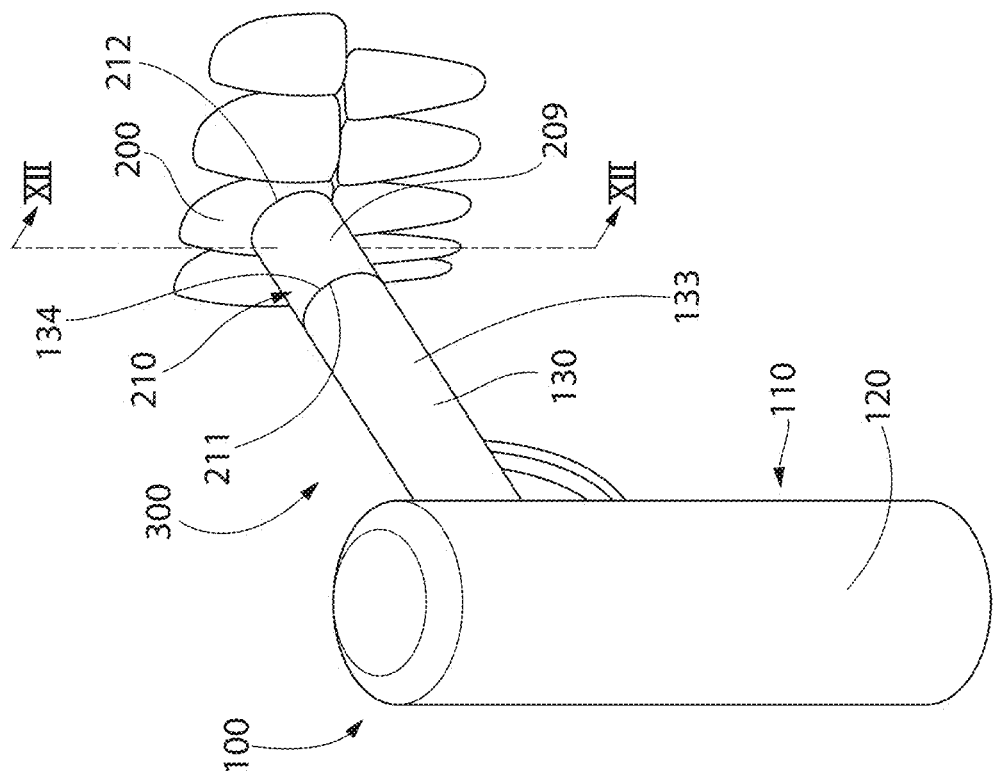
FIG. 11 is a perspective view illustrating the color or shade measurement device having the spacer thereto as shown in FIG. 10 being used to take a measurement of a shade or color of a tooth.

Referring to FIGS. 11 and 12, the tooth assessment system 300 is illustrated during use with the spacer 210 in the second state (i.e., coupled to the probe portion 130). In order to use the tooth assessment system 300 to measure a color or shade of a tooth when the spacer 210 is in the second state, the distal end 212 of the sleeve 209 of the spacer 210 is placed into contact with the tooth 200. When the tooth assessment system 300 is used with the spacer 210 in the second state, the light emitted by the distal end 132 of the probe portion 130 does not penetrate beyond the enamel layer 201 of the tooth 200. Some of the light may contact an exposed outer surface 203 of the tooth 200 and then be returned to the light receiver 175 at the distal end 132 of the probe portion 130 and some of the light may penetrate the enamel layer 201 of the tooth 200 without penetrating the dentin layer 202 of the tooth 200 before being returned to the light receiver 175 at the distal end 132 of the probe portion 130.

More specifically, in the exemplified embodiment the light emitted from the plurality of light emitters 153 of the first array of light emitters 155 may contact the exposed outer surface 203 of the tooth 200 and then be returned to the light receiver 175. Furthermore, in the exemplified embodiment the light emitted from the plurality of light emitters 154 of the second array of light emitters 156 may penetrate the enamel layer 201 of the tooth 200 without penetrating beyond the enamel layer 201 and into the dentin layer 202 of the tooth 200 before being returned to the light receiver 175. Thus, the depth of penetration of the light is reduced when the spacer 210 is coupled to the probe portion 130 because the distal end 132 of the probe portion 130 from which the light is emitted is spaced a greater distance from the tooth 200 when the spacer 210 is attached. Of course, depending on the arrangement of the plurality of first and second light emitters 153, 154, the tooth assessment system 300 may be configured so that when the spacer 210 is in the second state, none of the light emitted from the distal end 132 of the probe portion 130 penetrates the exposed outer surface 203 of the tooth 200. Rather, it may be possible to ensure that all light emitted merely contacts the exposed outer surface 203 of the tooth 200 and is then returned to the distal end 132 of the probe portion 130 for analysis of the shade or color of the tooth 200. This may be desirable to detect effectiveness of an instant whitening formulation as noted above, although its effectiveness may be detected even if some of the light does penetrate the enamel layer 201 so long as it does not penetrate the dentin layer 202.

Comparing operation when the spacer 210 is in the first state as shown in FIG. 6 and with the spacer 210 in the second state as shown in FIG. 12, in the first state (spacer not attached, FIG. 6) the light emitted from the distal end 132 of the probe portion 130 penetrates a first average depth into the tooth 200 and in the second state (spacer attached, FIG. 12) the light emitted from the distal end 132 of the probe portion 130 penetrates a second average depth into the tooth 200. As should be appreciated, the first average depth is greater than the second average depth. Thus, when the spacer 210 is coupled to the probe portion 130, the light penetrates less of a depth into the tooth 200 than when the spacer 210 is not coupled to the probe portion 130.

Figure 13:
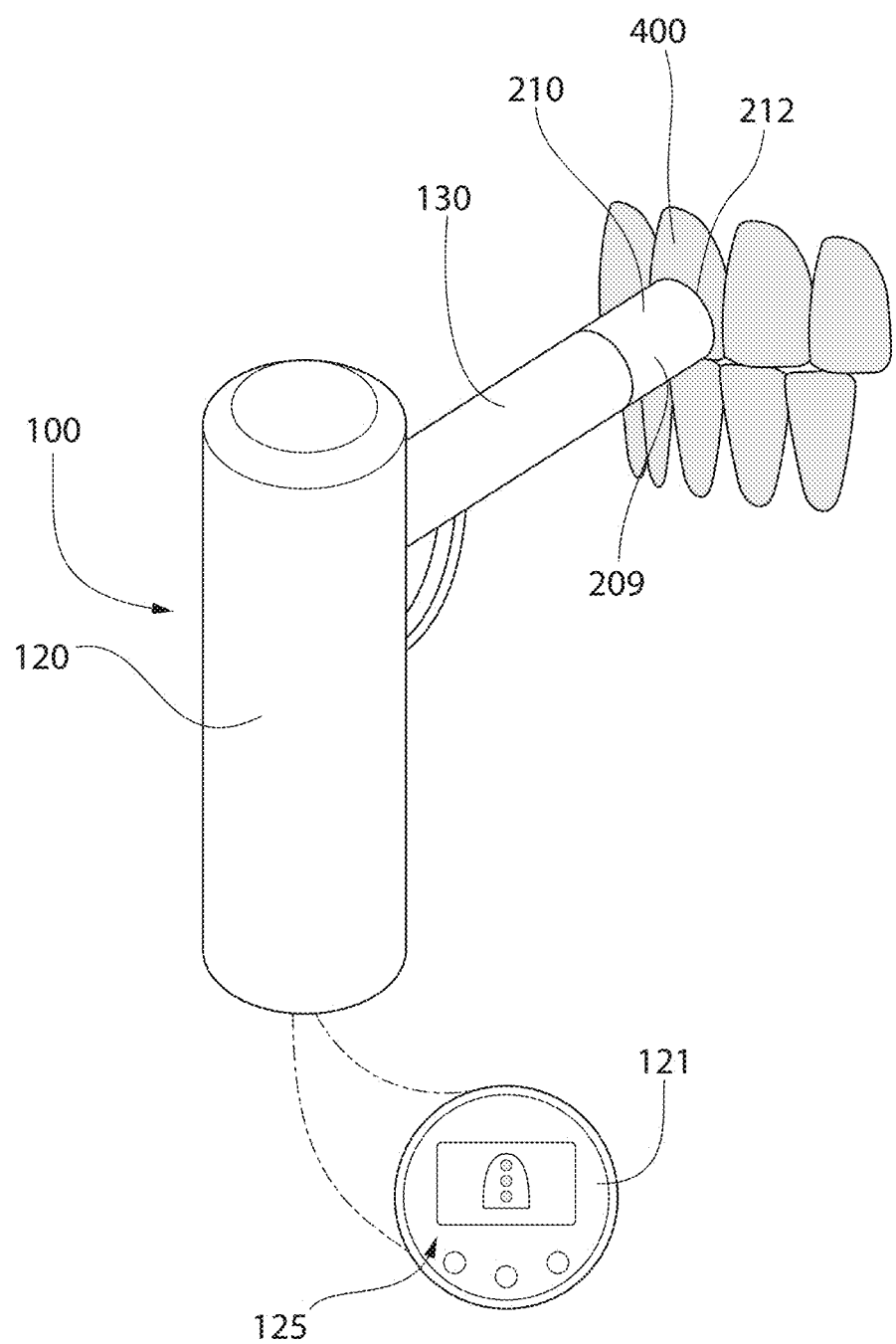
FIG. 13 is a perspective view illustrating the color or shade measurement device having the spacer thereto as shown in FIG. 10 being used to take a measurement of a shade or color of a tooth before application of a tooth whitening formulation thereon.
Figure 14:
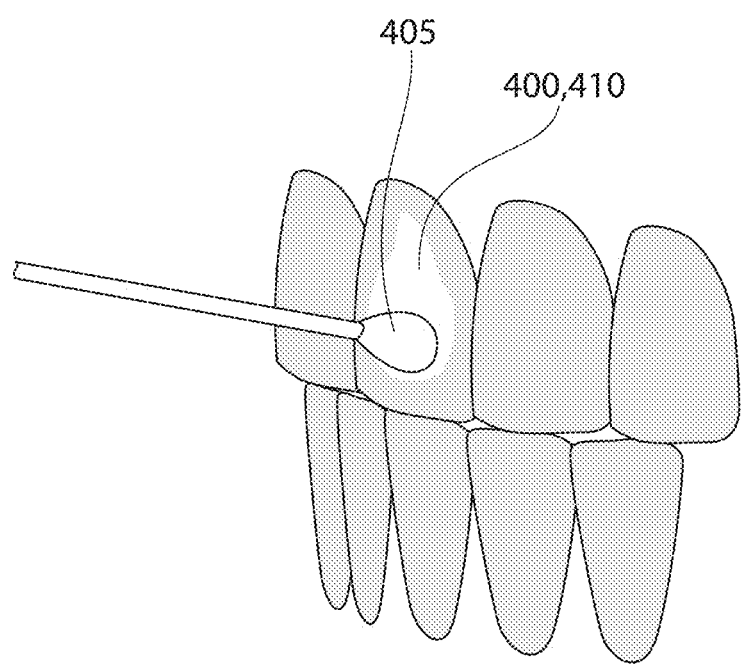
FIG. 14 is a perspective view illustrating a tooth whitening formulation being added to the tooth of FIG. 13.
Figure 15:
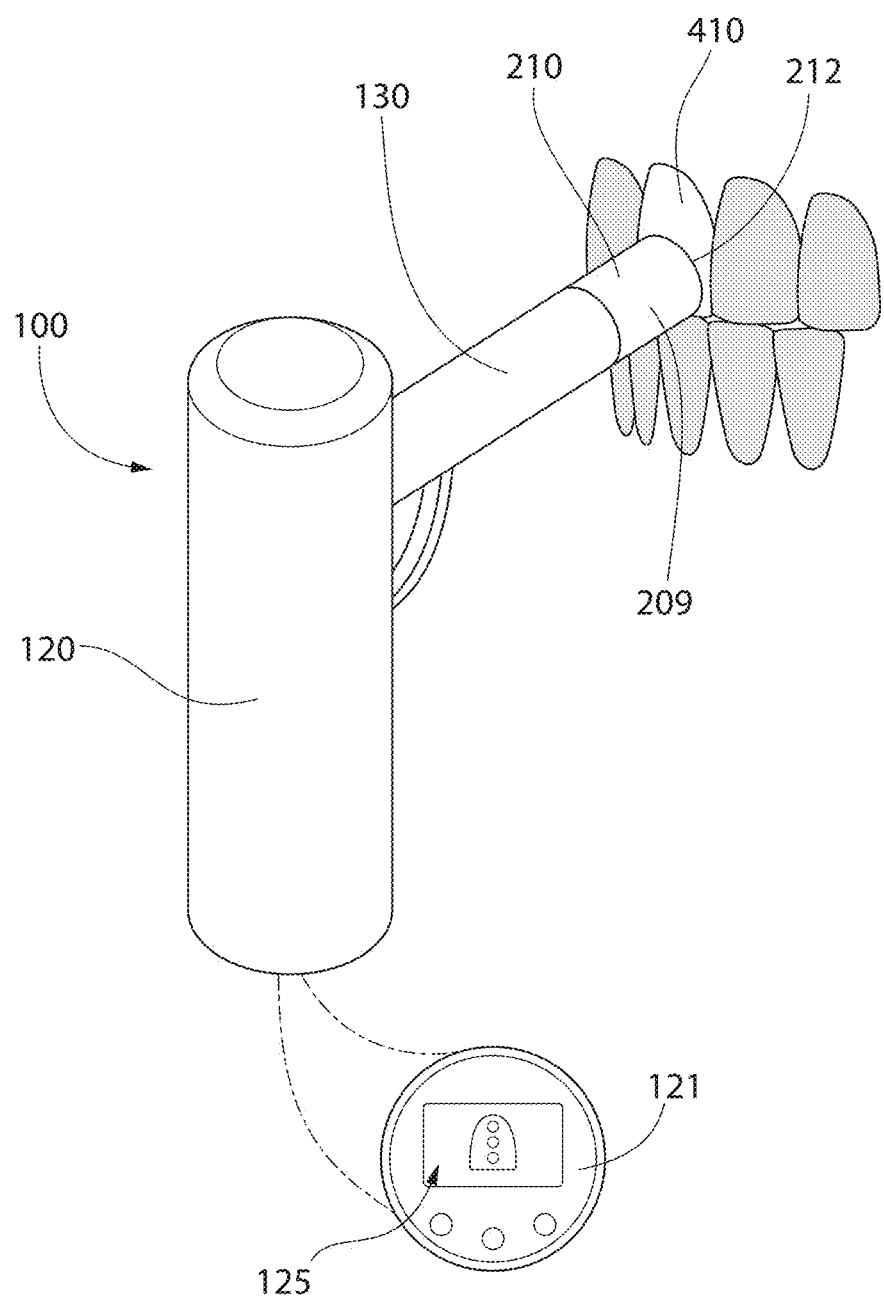
FIG. 15 is a perspective view illustrating the color or shade measurement device having the spacer thereto as shown in FIG. 10 being used to take a measurement of a shade or color of the tooth after application of the tooth whitening formulation thereon.

Referring to FIGS. 13-15, a method of assessing tooth color or shade using the color measurement device 100 and the spacer 210 will be described with particular regard to determining the effectiveness of an instant tooth whitening formulation. As noted above, the color measurement device 100 is not limited to detecting color or shade of teeth, although that is one possible use. However, the color measurement device 100 may have other uses, for example in the measurement of skin color or the like.

FIG. 13 illustrates the color measurement device 100 illustrated in the previous figures and described above being used to measure a color or shade of an untreated tooth 400 with the spacer 210 in the second state (i.e., attached to the probe portion 130). First the color measurement device 100 described above is provided. Next, the spacer 210 is coupled to the probe portion 130 of the color measurement device 100 as described above. The distal end 212 of the spacer 210 (which protrudes from the distal end 132 of the probe portion 130) is then placed into contact with the exposed outer surface of the untreated tooth 400. Next, the light emitter assembly 150 is activated so that light is generated by the light emitter assembly 150 and emitted from the distal end 132 of the probe portion 130. As discussed above with reference to FIG. 12, this light does not penetrate beyond the enamel layer of the untreated tooth 400. Rather, the light either contacts the exposed outer surface of the untreated tooth 400 and is then returned to the distal end 132 of the probe portion 130 or the light penetrates into the enamel layer of the untreated tooth 400 without passing into the dentin layer of the untreated tooth 400. Thus, with the spacer 210 coupled to the probe portion 130, the light emitted from the distal end 132 of the probe portion 130 does not penetrate beyond the enamel layer of the untreated tooth 400.

Next, the light receiver assembly 170 of the color measurement device 100 receives at least a portion of the emitted light as it is returned to the distal end 132 of the probe portion 130. The light receiver assembly 170 then generates data indicative of a color or a shade of the untreated tooth based on the received light. The color measurement device 100 may display information indicative of the color or the shade of the tooth on the display 125 which either forms a part of the color measurement device 100 (as shown in the exemplified embodiment) or is located on a device that is separate from the color measurement device 100. The displayed information may be relevant to a known tooth color or shade scale or guide so that the data is quantifiable and can be understood by the user.

Next referring to FIG. 14, a user may apply a tooth whitening formulation 405 to the untreated tooth 400 to form a treated tooth 410. Specifically, the treated tooth 410 is the untreated tooth 400 with the tooth whitening formulation 405 adhered thereto or otherwise positioned thereon. The tooth whitening formulation 405 may in some embodiments be an instant tooth whitening formulation such as has been described herein above. Of course, other agents that may improve the results of the measurements using the color or shade measurement device 100 with the spacer 210 thereon may be used in place of a tooth whitening formulation in alternative embodiments.

Finally, referring to FIG. 15, the testing is repeated again on the same tooth (which is now the treated tooth 410). Specifically, the distal end 212 of the spacer 210 is placed into contact with the exposed outer surface of the treated tooth 410 and the light emitting assembly 150 is activated. The light emitting assembly 150 generates light and emits the light from the distal end 132 of the probe portion 130. Again, the light does not penetrate beyond the enamel layer of the treated tooth 410. Stated another way, the emitted light does not penetrate into the dentin layer of the treated tooth 410. Rather, the light either hits the exposed outer surface of the treated tooth 410 without penetrating the treated tooth 410 at all, or the light penetrates into the enamel layer of the treated tooth 410 without also penetrating into the dentin layer of the treated tooth 410.

After the light contacts the treated tooth 410, it is returned to the distal end 132 of the probe portion 130 where it is received by the light receiver 175. The received light is then analyzed and data is generated indicative of a color or a shade of the treated tooth in accordance with a tooth color or shade scale or guide so that the data is quantifiable and can be understood by the user. The data may be displayed on the display 125 that is either located on the color measurement device 100 or is a part of a separate display device (i.e., screen, computer, laptop, smart phone, etc.). A user can compare the data from the untreated tooth with the data from the treated tooth to determine the effectiveness of the tooth whitening formulation 405. For example, the tooth color or shade scale may be a scale of 1 to 20 with 1 being the whitest and 20 being the darkest. During the test of the untreated tooth, the data may indicate that the tooth color or shade is a 17. During the test of the treated tooth, the data may indicate that the tooth color or shade is a 3. Thus, a user will have a quantifiable understanding of the effectiveness of the tooth whitening formulation (i.e., the tooth whitening formulation whitened the teeth by 14 shades, etc.).

Even though the tooth whitening formulation 405 may only coat an exterior surface of the treated tooth 410, the color measurement device 100 with the spacer 210 coupled thereto will be able to discern the difference in color/shade because its emitted light only penetrates so far as the enamel layer and not the dentin layer. The difference in color/shade would not be detected as effectively with the color measurement device 100 without the spacer 210 coupled thereto because the light will penetrate too far into the treated tooth 410 such that the light being analyzed by the light receiver assembly 170 will not be indicative of the portion of the treated tooth 410 that has the tooth whitening formulation 405 thereon. Thus, only with the spacer 210 coupled thereto can the color measurement device 100 accurately detect changes in tooth shade/color that are based on instant tooth whitening formulations that merely coat an exterior of the tooth.

Thus, the color measurement device 100 with the spacer 210 coupled thereto (i.e., in the second state) can be used at trade shows and demonstrations to illustrate to a user (with immediate results) the effectiveness of the tooth whitening formulation 405 in a manner that is readily understandable by the user. Additionally, the color measurement device 100 with the spacer 210 coupled thereto can be used at a dentist's office or at home to quantify the results of a tooth whitening formulation that coats the exterior of the tooth without actually changing the color/shade of the interior of the tooth.

The terms color and shade are used herein fairly interchangeably. With regard to teeth, color is typically discussed in terms of shade and thus the terms color and shade have a similar meaning. However, as a general matter the terms color and shade may have different meanings, particularly in different technology areas. Specifically, the term shade may refer to a variety of a particular color (i.e., shades of red, shades of yellow, shades of green, etc.). Regardless, as used herein, the color or shade measurement device 100 is configured to measure either color or shade or both color and shade of a particular object.

In certain embodiments, the length of the spacer used for a particular assessment is dictated by the intensity of the light emitted from the color or shade measurement device. Thus, a device that emits a higher intensity of light might require a longer spacer to ensure that the light is not penetrating beyond the enamel of the tooth whereas a device that emits a lower intensity of light might require a shorter length spacer to ensure that the emitted light is reaching the enamel without penetrating it. Thus, in certain embodiments the spacer and the light emitter assembly are configured to ensure that without the spacer the light penetrates the enamel and dentin layers of a tooth and with the spacer the light does not penetrate beyond the enamel layer.

Figure 18:
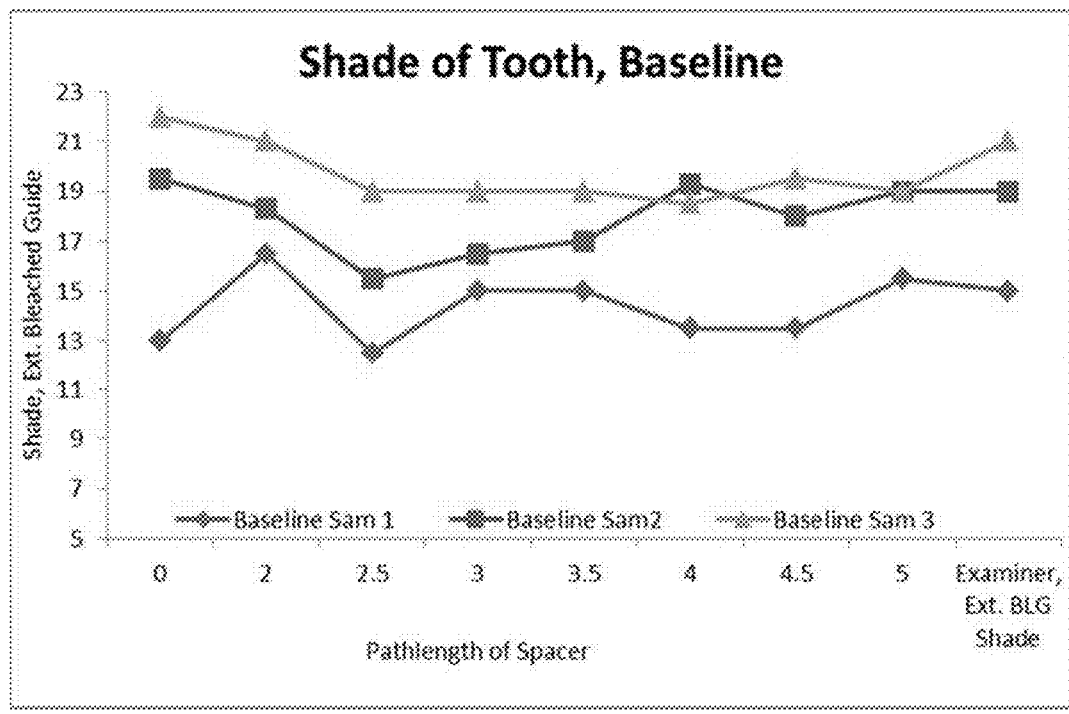
FIG. 18 is a graph of the Before Treatment portion of the table of FIG. 17.
Figure 19:
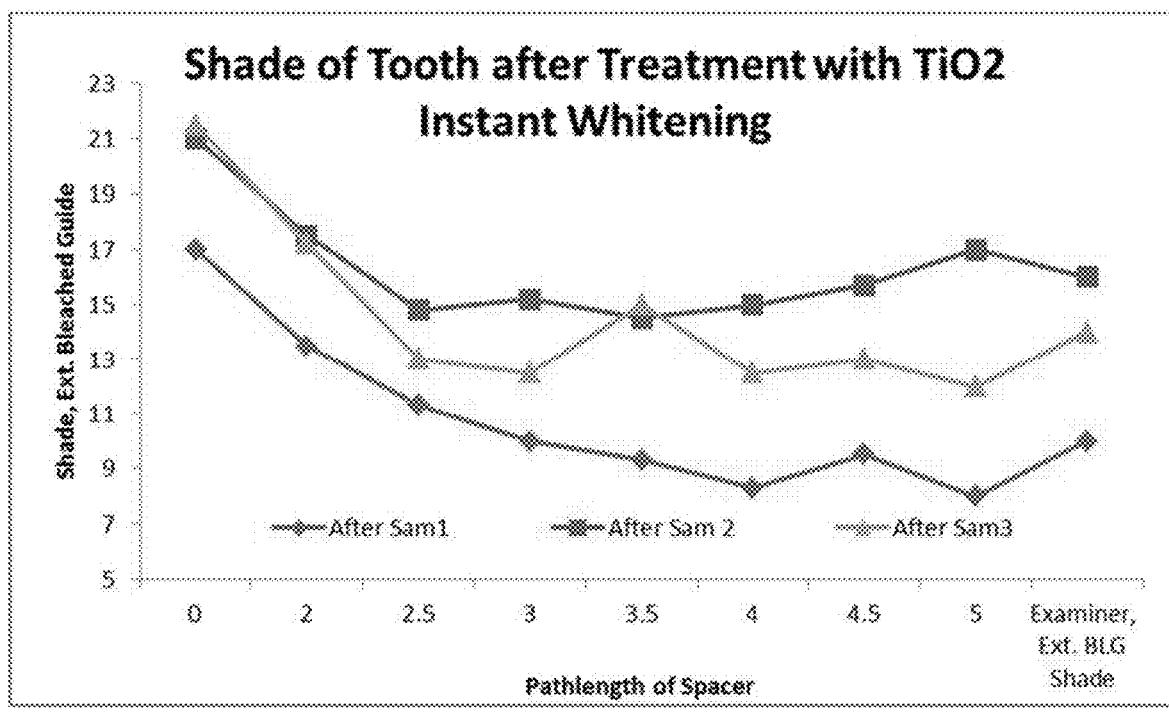
FIG. 19 is a graph of the After Treatment portion of the table of FIG. 17.

Referring to FIGS. 17-19, experimental results using the color or shade measurement device 100 with spacers of different length both before and after treatment of a tooth will be described. In the FIG. 17 table, the pathlength is the difference between L2 and L1 rather than being the total length of the spacer. Thus, the pathlength of zero is when the color or shade measurement device 100 is used without any spacer, the pathlength of 2 is when the color or shade measurement device 100 is used with a spacer such that the length L2 of the spacer is 2 mm greater than the length L1 of the second portion 135 of the probe portion 130, and so on. There were three tooth samples used in the experiment, referred to as Sample 1, Sample 2, and Sample 3 (i.e., Sam 1, Sam 2, Sam 3 in the table of FIG. 17). The numerical values in the chart are the measured shade in units of extended bleached guide, which is a guide having numerical values from 1-29. The lower the number, the whiter the tooth. The column Examiner, Ext. BLG Shade is the shade value determined by visual inspection rather than using the color or shade measurement device 100. Thus, this is a comparative value for purposes of determining which spacer length achieved measurements that most closely match the value obtained via visual inspection. The spacers in the experiment were created using a 3D printer and the objective of the experiment was to identify the optimal pathlength for measurement of surface color after treatment of a tooth with an instant whitening product.

The methodology of the experiment will now be described. Three human tooth samples were measured with each of the spacers using a VITA EasyShade® device, available from VITA, in ambient conditions in its normal operating state. The spacers were created with 3D printing and made with hard plastic composite material for strength and durability. The tooth samples were rewetted between measurements to ensure the surface moisture content remained constant during the study. Excess moisture was removed before the analysis with a damp cloth. Replicate measurements were made on the tooth surface and the results were averaged.

After baseline measurements were made (top portion of FIG. 17 labeled "Before Treatment" and graph of FIG. 18), the teeth were treated with a paint-on instant whitening product containing 1.5% TiO2. After drying, the teeth were stored in water between measurements. Before each measurement, the spacer was placed on the tip of the Easyshade® probe. The device was calibrated with a 100% reflective white tile and then used to measure the surface of the tooth.

FIGS. 17-19 show the results before and after treatment. The data without a spacer (i.e., pathlength of 0) shows the Easyshade® device not detecting the presence of the instant whitening product. The results are similar before and after measurement because the depth of measurement of 1.41 mm and 2.8 mm for the inner and outer array respectively (based on the physics of the optical components—as shown in FIG. 16B) focuses the light well beneath the surface of the tooth. Based on the geometry shown, the theoretical optimal pathlength for the outer array to measure surface color is 2.8 mm (approx. 3 mm). The data shown in the table demonstrates the optimal pathlength based on comparing the result with the examiner assessment (i.e., visual assessment) of color was found to be close to 3 mm (i.e., L2−L1 being approximately 3 mm was optimal for purposes of this study). Increasing pathlength beyond this thickness did not improve the agreement between the device measurement and the Examiner measurement. It should be noted that it is possible that different tooth whitening technologies may require different spacers, and thus, an optimization experiment may be required to identify the optimal spacer requirements for different tooth whitening technologies.

FIGS. 18 and 19 graphically demonstrates the data found in the table of FIG. 17. Shade in units of extended bleached guide (1-29) is plotted as a function of pathlength for the baseline measurements and after treatment measurements.

The invention of using a spacer allows the use of the low cost in-office EasyShade® whitening measurement device to measure shade change in units of Extended Bleached Guide, after use of cosmetic products intended to instantly deliver a whitening benefit to the surface of the tooth. In this example, a value of L2–L1 of approximately 3 mm delivers optimal results, but other L2–L1 lengths (and hence other spacer lengths) may be needed for other surface color changing technologies. An array of spacers may be developed and sold for use with this device to cover potential future applications.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A tooth assessment system comprising:
   a color or shade measurement device comprising:
      a probe portion terminating at a distal end;
      a light emitter assembly configured to generate and emit light from the distal end of the probe portion;
      a light receiver assembly configured to receive a portion of the light that has been emitted from the distal end of the probe portion and returned to the distal end of the probe portion as received light and generate data indicative of a color or a shade based on the received light;
   a spacer detachably coupled to the probe portion so as to be alterable between a first state in which the spacer is detached from the probe portion and a second state in which the spacer is coupled to the probe portion and protrudes beyond the distal end of the probe portion; and
   wherein the spacer and the light emitter assembly are configured such that: (1) in the first state, the light emitted from the distal end of the probe portion penetrates into both an enamel layer and a dentin layer of a tooth when the distal end of the probe portion is placed into contact with the tooth; and (2) in the second state, the light emitted by the distal end of the probe portion does not penetrate beyond the enamel layer of the tooth when a distal end of the spacer is placed into contact with the tooth.

2. The system according to claim 1 wherein in the first state the light emitted from the distal end of the probe portion penetrates a first average depth into the tooth and in the second state the light emitted by the distal end of the probe portion penetrates a second average depth into the tooth, the first average depth being greater than the second average depth.

3. The system according to claim 1 wherein in the second state at least a portion of the light from the light source contacts an exposed outer surface of the tooth without penetrating the exposed outer surface of the tooth.

4. The system according to claim 1 wherein the light receiver assembly comprises at least one light receiver located at the distal end of the probe portion and wherein the light emitter assembly comprises a first array of light emitters located at the distal end of the probe portion and surrounding the at least one light receiver and a second array of light emitters located at the distal end of the probe portion and surrounding the first array of light emitters.

5. The system according to claim 4 wherein in the first state the light emitted from the first array of light emitters does not penetrate beyond the enamel layer of the tooth and the light emitted from the second array of light emitters penetrates into the dentin layer of the tooth when the distal end of the probe portion is placed into contact with the tooth, and wherein in the second state the light emitted from the first array of light emitters contacts an exposed outer surface of the tooth without penetrating the tooth and the light emitted from the second array of light emitters penetrates into the enamel layer of the tooth without penetrating into the dentin layer of the tooth when the distal end of the spacer is placed into contact with the tooth.

6. The system according to claim 1 wherein the color or shade measurement device further comprises a body portion, the probe portion comprising a first portion extending from the body portion to a distal end and a second portion extending from the distal end of the first portion to the distal end of the probe portion, the first portion having a first minimum diameter and the second portion having a second maximum diameter, the first minimum diameter being greater than the second maximum diameter.

7. The system according to claim 6 wherein the spacer comprises a sleeve extending along a longitudinal axis from a proximal end to a distal end, the sleeve having an inner surface defining a central passageway that extends from a first opening at the proximal end of the sleeve to a second opening at the distal end of the sleeve, and wherein in the second state at least a portion of the probe portion extends into the central passageway of the sleeve and the distal end of the probe portion is located between the proximal and distal ends of the sleeve.

8. The system according to claim 7 wherein the spacer is coupled to the second portion of the probe portion via frictional engagement between the inner surface of the sleeve and an outer surface of the second portion of the probe portion.

9. The system according to claim 7 wherein the second portion of the probe portion has a first length measured from the distal end of the first portion of the probe portion to the distal end of the probe portion and wherein the spacer has a second length measured from the proximal end of the sleeve to the distal end of the sleeve, the second length being greater than the first length.

10. The system according to claim 1 wherein the data generated by the light receiver assembly is indicative of a shade of the tooth, and wherein the color or shade measurement device further comprises a housing and a display on the housing for displaying information indicative of the shade of the tooth based on the data generated by the light receiver assembly.

11. The system according to claim 1 wherein the light emitter assembly comprises a light source and a fiber optic subassembly extending from the light source to the distal end of the probe portion.

12. The system according to claim 1 wherein the light receiver assembly comprises a spectrometer.

13. A tooth assessment system comprising:
   a color or shade measurement device comprising:
   a probe portion terminating at a distal end;
   a light emitter assembly configured to generate and emit light from the distal end of the probe portion;
   a light receiver assembly configured to receive a portion of the light that has been emitted from the distal end of the probe portion and returned to the distal end of the probe portion as received light and generate data indicative of a color or a shade based on the received light;
   a spacer comprising a sleeve extending from a proximal end to a distal end and defining a central passageway, the spacer alterable between: (1) a first state in which the spacer is detached from the probe portion; and (2) a second state in which at least a portion of the probe portion extends into the central passageway of the sleeve and the distal end of the probe portion is located between the proximal and distal ends of the sleeve;
   wherein the spacer is formed of a rigid material and wherein the probe portion comprises a first portion extending from a first end to a second end and a second portion extending from the second end of the first portion to the distal end of the probe portion, the first portion having a first minimum diameter and the second portion having a second maximum diameter, the first minimum diameter being greater than the second maximum diameter; and
   wherein the spacer and the light emitter assembly are configured such that: (1) in the first state, the light emitted from the distal end of the probe portion penetrates into both an enamel layer and a dentin layer of a tooth when the distal end of the probe portion is placed into contact with the tooth; and (2) in the second state, the light emitted by the distal end of the probe portion does not penetrate beyond the enamel layer of the tooth when the distal end of the sleeve is placed into contact with the tooth.

14. The system according to claim 13 wherein the second end of the first portion of the probe portion forms an annular shoulder that protrudes radially from the second portion of the probe portion, and wherein in the second state the proximal end of the sleeve is in surface contact with the annular shoulder of the first portion of the probe portion and the distal end of the sleeve extends beyond the distal end of the probe portion.

15. The system according to claim 13 wherein in the second state the spacer is coupled to the second portion of the probe portion via frictional engagement between an inner surface of the sleeve that defines the central passageway and an outer surface of the second portion of the probe portion.

16. The system according to claim 13 wherein the central passageway extends from a first opening at the proximal end of the sleeve to a second opening at the distal end of the sleeve, and wherein in the second state an entirety of the second portion of the probe portion is located within the central passageway of the sleeve.

17. The system according to claim 16 wherein the central passageway of the sleeve has a constant diameter from the proximal end of the sleeve to the distal end of the sleeve.

18. A method of assessing tooth color or shade, the method comprising:
   a) providing a color or shade measurement device comprising: a probe portion terminating at a distal end; a light emitter assembly configured to generate and emit light from the distal end of the probe portion; and a light receiver assembly configured to: (1) receive a portion of the light that has been emitted from the distal end of the probe portion and returned to the distal end of the probe portion as received light; and (2) generate data indicative of a color or a shade based on the received light, wherein when the distal end of the probe portion is placed into contact with the tooth and the light emitter assembly is activated, the light emitted by the distal end of the probe portion penetrates into both an enamel layer and a dentin layer of a tooth;
   b) coupling a spacer to the probe portion so that the spacer protrudes beyond the distal end of the probe portion;
   c) contacting a surface of a tooth with a distal end of the spacer and activating the light emitter assembly such that the light emitted from the distal end of the probe portion does not penetrate beyond the enamel layer of the tooth;
   d) receiving, with the light receiver assembly, at least a portion of the light emitted in step c); and
   e) generating data indicative of a color or a shade of the tooth based on the light received in step d).

* * * * *